(12) United States Patent
Frank et al.

(10) Patent No.: US 6,720,161 B1
(45) Date of Patent: Apr. 13, 2004

(54) IMMOBILIZED SUBSTRATE, SEPARATION GELS AND METHOD FOR DETECTING ENZYMATIC ACTIVITY

(75) Inventors: Ronald Frank, Braunschweig (DE); Werner Tegge, Braunschweig (DE)

(73) Assignee: Gesellschaft fuer Biotechnologische Forschung mbH, Braunschweig (DE)

( * ) Notice: Subject to any disclaimer, the term of this patent is extended or adjusted under 35 U.S.C. 154(b) by 0 days.

(21) Appl. No.: 09/673,337

(22) PCT Filed: Apr. 21, 1999

(86) PCT No.: PCT/EP99/02688

§ 371 (c)(1),
(2), (4) Date: Dec. 26, 2000

(87) PCT Pub. No.: WO99/54729

PCT Pub. Date: Oct. 28, 1999

(30) Foreign Application Priority Data

Apr. 22, 1998 (DE) ......................................... 198 18 077

(51) Int. Cl.⁷ ................................................. C12Q 1/48
(52) U.S. Cl. .............................................. 435/15; 435/4
(58) Field of Search ....................................... 435/4, 15

(56) References Cited

U.S. PATENT DOCUMENTS 4,824,778 A * 4/1989 Nagai et al.
6,228,998 B1 * 5/2001 Miura et al.

OTHER PUBLICATIONS

WO 97/25437. Te Koppele et al., 1997. Method for assaying proteolytic enzymes using fluorescence–quenched substrates.*

\* cited by examiner

*Primary Examiner*—Ralph Gitomer
(74) *Attorney, Agent, or Firm*—Frommer Lawrence & Haug LLP; Ronald R. Santucci

(57) ABSTRACT

The present invention refers to a method for attaching substrate molecules to gel matrices, characterized in that a substrate is covalently bound to a monomeric or oligomeric constitutional unit of a gel and the resultant product is polymerized. The present invention further refers to gels obtainable by this process.

14 Claims, 4 Drawing Sheets

A

B

Figure 1:
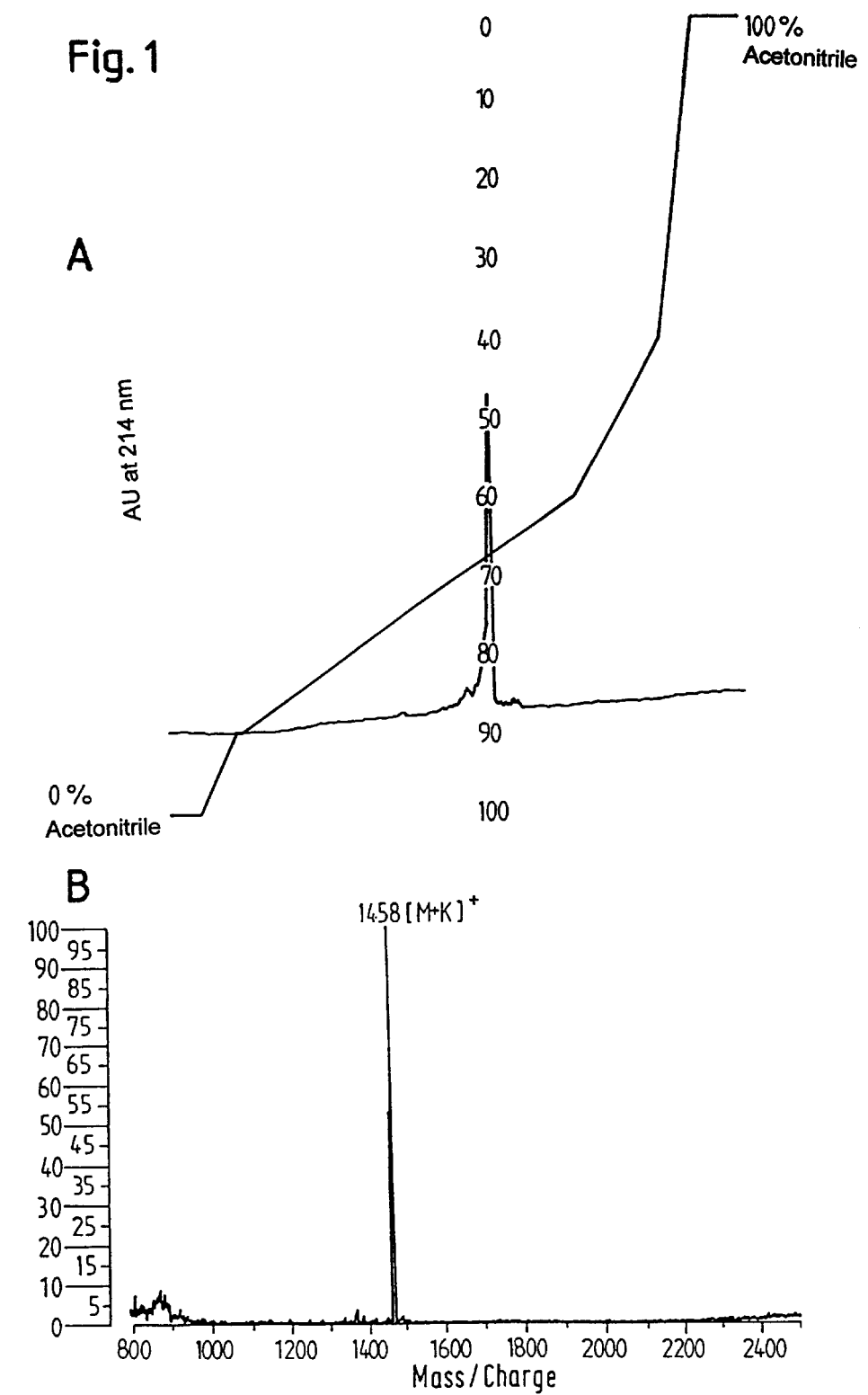

IMMOBILIZED SUBSTRATE, SEPARATION GELS AND METHOD FOR DETECTING ENZYMATIC ACTIVITY

This application is a 371 of PCT/EP99/02688 filed Apr. 21, 1999 which claims priority to Germany 198 18 077.2 filed Apr. 22, 1998.

Electrophoresis using gels of polyacrylamide, agarose, starch, etc., is state of the art for high resolution separation of complex mixtures of proteins, e. g., of cell extracts or of synthetic reaction mixtures (chemical synthesis, biological synthesis such as in vitro translation); (cf. G. M. Rothe, Electrophoresis of Enzymes—Laboratory Models, 1994, Springer Verlag, Berlin). Electrophoretical separation methods comprise electrophoresis, isotachophoresis, and isoelectric focussing. In particular, electrophoresis is conducted in a denaturating medium (in the presence of SDS, urea, guanidinium salts, mercaptoethanol, etc.) whereby the protein chains unfold and a separation mainly according to the size of the molecules is achieved. This denaturation, of course, eliminates any biological activity (ligand binding, substrate binding and substrate transformation) of the protein components. However, proteins can be refolded to their active, natural structure by a renaturation procedure. This renaturation can be conducted directly in the gel (ibid, p. 135 ff.). If the proteins are large compared to the pore structure of the gel matrix then the proteins remain localized at the separation position without substantially reducing the resolution of separation. The enzyme proteins can then develop their activity with respect to a substrate which is diffused into the gel after electrophoretic separation and optional renaturation or which was added to the gel before its polymerization (ibid, p. 165, ff.). The product of this enzyme reaction can be used to locally characterize and identify the enzyme if this product also remains localized in the gel at the (same) position at which the reaction takes place. A large number of such reactions have been described (ibid, p. 141, ff.) for which, however, the following restrictions are valid:

a) The substrate is small compared to the pore structure of the gel and is diffused into the gel after electrophoretic separation and optional renaturation; the enzyme reaction is then detected by the formation of a colored, insoluble (i. e., locally precipitating) product.

b) the substrate is large compared to the pore structure of the gel and is added to the gel before its polymerization; the product of the enzyme reaction remains large and is detected accordingly or the substrate is degraded into small fragments which are eluted out of the gel and the enzyme activity is detected as the absence of the substrate at the respective position (negative staining).

The choice of employable substrate molecules for the method in these embodiments, however, is very restricted due to the various specific requirements the substrate and the product, respectively, have to fulfill. Many enzymes can convert small substrates as well and can convert a large variety of synthetically accessible substrates as well. The products of these reactions cannot be adapted to the above requirements for in situ detection in the gel. As a possibility to use such substrates in a flexible way, e. g., Kameshita and Fujisawa have described covalent binding with a large carrier molecule (Anal. Biochem., 1996, Vol. 237, pp. 198–203). This is based on the same principle as described in item b), namely physical entrapment of the substrate conjugate in the matrix of the gel.

To detect protein kinases short synthetic oligopeptides, which had a cysteine unit at the N-terminus, were covalently bound to various polyamino acids having a size of 23 000 to 198 200 Dalton using the bifunctional reagent N-(-maleimidocaproyl) succinimide. In this manner, it was possible to detect the catalytical subunits of the cAMP dependent protein kinase (PKA), CaM kinase II and CaM kinase IV together with the synthetic peptide substrates Kamptide (CLRRWSVA), C-Syntide-2 (CPLARTLSVAGLLPLKK) and CAMKAKS (CSQPSFQWRQPSLDVDVGD) in the gel after radioactive phosphorylation in the presence of [$\gamma$-$^{32}$P] ATP and autoradiography. (These peptides are given in the one-letter-code with the N-terminus on the left hand side and the C-terminus on the right hand side.) However, it was observed that the kind of carrier molecule, in this case: its composition of amino acid units, influences the use of the substrate and that the carrier molecule itself can function as a substrate, respectively. The second possibility is very undesirable under specific circumstances if the enzymes are to be detected selectively and specifically.

The object of the present invention is to provide an improved method and an improved gel for detecting and separating enzyme activities which overcomes the disadvantages of the state of the art and particularly overcomes the limitations connected with the choice of the substrate and the negative influence of the carrier molecules.

This object is achieved by a method for attaching substrate molecules to gel matrices characterized in that a substrate is covalently bound to a polymerizable monomeric or oligomeric constitutional unit of a gel and the resultant product, i.e., the constitutional units of the gel, is polymerized.

Preferably, the substrate is a natural or synthetic (oligo) peptide, a natural or synthetic (oligo)nucleotide or a DNA fragment.

The monomeric or oligomeric constitutional units of the gel comprise conventional monomers or polymerizable oligomers for the preparation of gels, such as acrylic acid monomers and/or acrylic acid oligomers and/or methacrylic acid monomers and/or methacrylic acid oligomers. However, as described above, all other conventional constitutional units can also be employed which can be polymerized to a gel.

Preferably for the polymerization, constitutional units of substrate and gel are mixed with constitutional units of gel which do not include substrate components. Preferably, the ratio of constitutional units of substrate and gel to constitutional units of unmodified gel is chosen so that the amount of substrate in the gel is sufficient to detect the enzyme reaction. The polymerization can be a conventional type of polymerization such as solution or bulk polymerization.

According to a particularly preferred embodiment of the method according to the present invention a spacer (a bifunctional spacing molecule) is incorporated between the substrate and the monomeric or oligomeric constitutional unit of the gel and is covalently bound to both components.

Such a construction has the following constitution:

MONOMER–(SPACER)$_{optional}$–SUBSTRATE

MONOMER (M): e.g., acrylic acid, methacrylic acid, etc.

SPACER (Sp):—aminocarboxylic acid (e.g., $C_2$ to $C_{20}$), oligonucleotide, oligopeptide, polyethylene glycol, etc.).

SUBSTRATE (Sub): synthetic peptide, oligonucleotide, small organic molecule, etc.

The spacer can be a spacer which is conventionally used in peptide and nucleotide chemistry, such as a natural or synthetic (oligo)peptide or a natural or synthetic (oligo) nucleotide.

According to the present invention, the product which optionally contains a spacer and which contains a constitutional unit of at least one substrate and least one gel unit is added to unmodified gel monomers or a solution of unmodified gel monomers, optionally mixed and then polymerized. During polymerization, the modified, monomeric or oligomeric unit containing at least one substrate and optionally at least one spacer is incorporated into the gel matrix just like the unmodified gel monomers and thereby the substrate is covalently bound to the gel matrix.

Furthermore, the present invention refers to a gel, which comprises immobilized substrates. This gel is preferably prepared as described above. It is particularly preferred that the gel is a separating gel.

The size of the pores and the cross-linking of the gel can be regulated in a conventional manner by varying the respective conditions of polymerization, such as the choice of the solvent, the concentration, the temperature, the use of a catalyst, etc.

An advantage of the localized attachment of the substrate which results and thus also of the product in the gel is that diffusion of the substrate/product is impossible and thus the high resolution of the gel is maintained.

EXAMPLES

Preparation of a Gel

A peptide having the sequence LRRASLG (Kemptide) was prepared by chemical synthesis according to the Fmoc method (G. B. Fields and R. L. Noble, Int. J. Peptide Protein Res., 1990, Vol. 35, pp. 161–214) on a TENTAGEL resin as a solid phase. The TENTAGEL resin is obtainable from Rapp Polymere (Tübingen, Germany) and contains a rink linker. This peptide sequence is a substrate for the catalytically active subunit of the cAMP dependent protein kinase (PKA) (B. E. Kemp and R. B. Pearson, 1991, Methods in Enzymology, Vol. 200, pp. 121–133). After incorporating the final (N-terminal) amino acid L, the peptide was extended by A, R, and A (Spacer). Then, the terminal amino group of the peptide was bound to acrylic acid (monomer for a polyacrylamide gel) via a carboxamide bond whereby the same chemical reaction was used as to bind the amino acid units to the peptide. The carrier and the protecting groups in the side chains of the amino acids were removed from the product in a conventional manner using trifluoroacetic acid and the product was purified by precipitation and preparative HPLC. Thus, the M-Sp-Sub-product is Acryl-A-R-A-L-R-R-A-S-L-G-NH$_2$.

Figure 2:
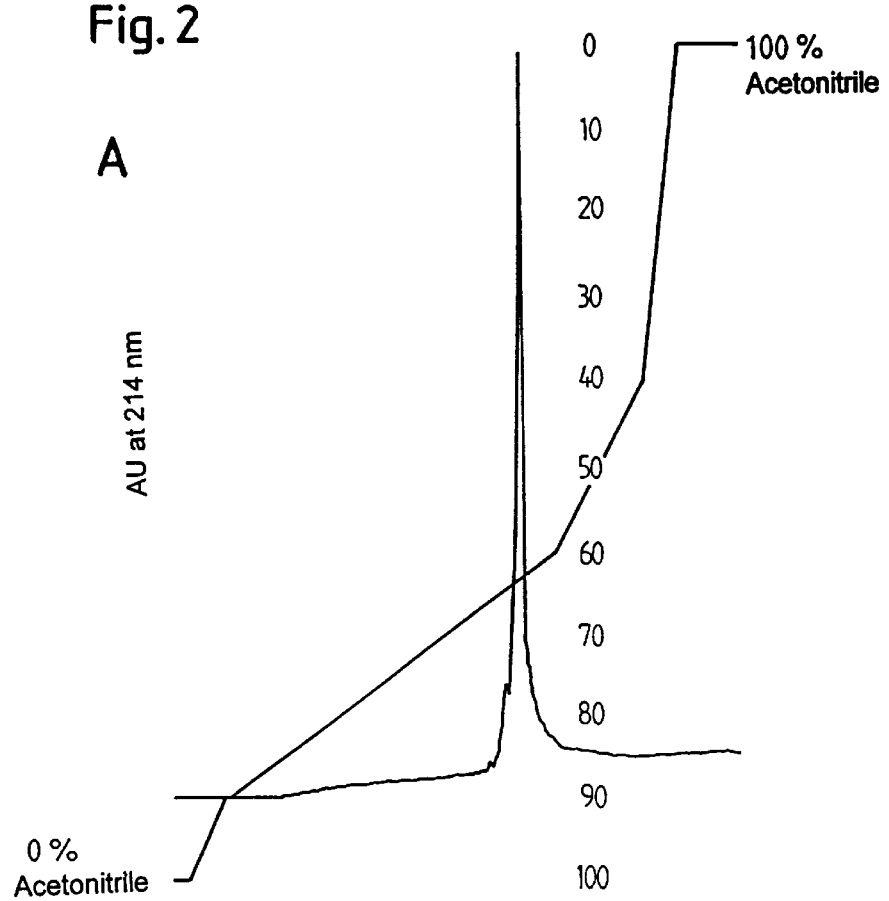
Figure 2:
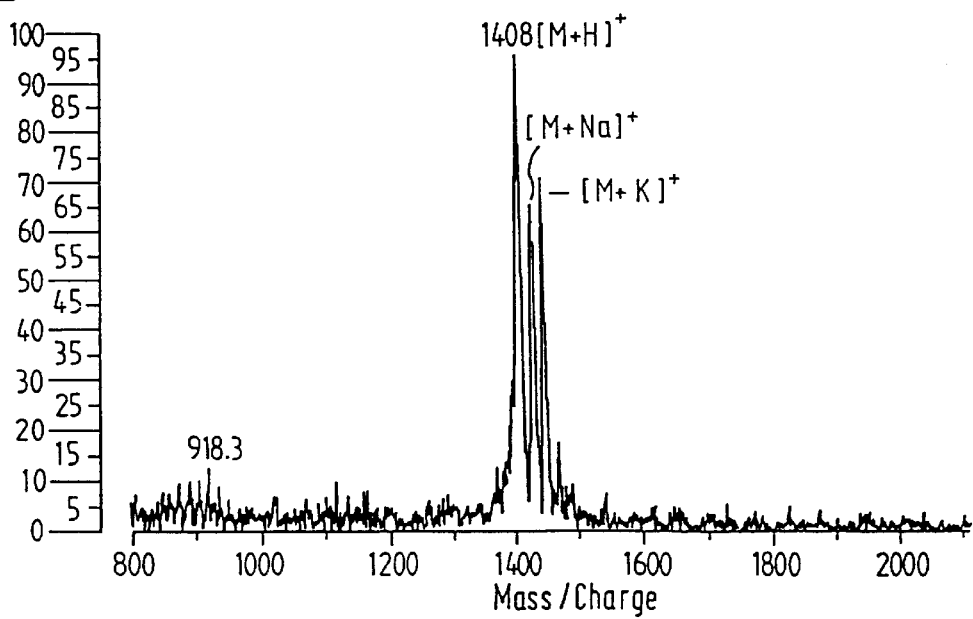

As a reference substrate, the same spacer-peptide sequence having an acetal group instead of an acrylic group was prepared. The identity and purity of the products was determined using analytical HPLC [C18-silica gel column ET 250/8/4 NUCLEOSIL 300-7 C$_{18}$ obtainable from Macherey-Nagel (Düren, Germany), gradient of acetonitrile with 0.1% trifluoroacetic acid to water with 0.1% trifluoroacetic acid as shown in FIG. 1A (acryl-peptide) and FIG. 2A (acetyl-peptide)] and MALDI-mass spectrometry of the main HPLC peak [Shimadzu-MALDI III, sinapic acid as a matrix, as shown in FIG. 1B (acryl-peptide) and FIG. 2B (acetyl-peptide)]. MW acryl-peptide=1419 theor.; MW acetyl-peptide=1407 theor.

The analytical data show that the desired compounds can be unambiguously prepared in high purity by methods known in peptide synthesis.

SDS polyacrylamide gel plates consisting of 10% separating gel and 3% spacer gel, respectively, were prepared according to the method of Laemmli (Nature 1970, Vol. 227, pp. 680–685).

The constructions of the substrate were added to the solutions for the separating gels at a concentration of 40 µg/ml before polymerization.

Separation of Protein Samples

The following protein samples were employed:

the catalytical subunit of the cAMP dependent protein kinase (PKA); 2.4 mg/ml.

a protein extract of murine embryonal stem cell line CCE (129/Sv/Ev derived) was prepared according to the method of Hipskind et al. (R. A. Hipskind, M. Baccarini and A. Nordheim, Molecular and Cellular Biology, 1994, Vol. 14, no. 9, pp. 6219–6231). The protein extract had a protein content of 2.8 mg/ml.

The amounts of protein given below were mixed with the application buffer according to Laemmli and separated by electrophoresis. The gels were treated according to the method of Kameshita and Fujisawa (Anal. Biochem., 1989, Vol. 183, pp. 139–143) after electrophoresis. The [γ-$^{32}$P] ATP had a specific activity of 185 TBq/mmol.

Figure 3:
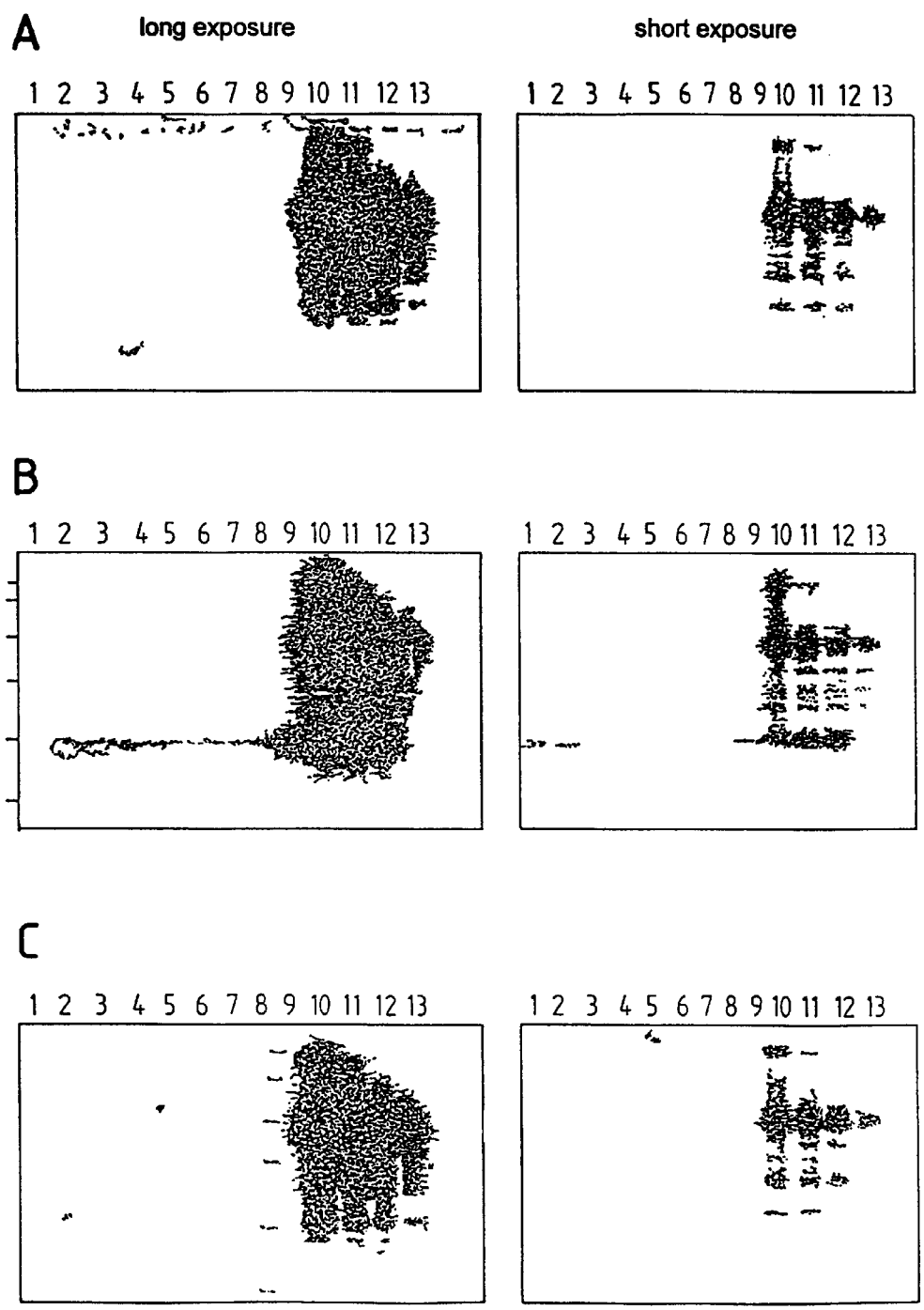

FIG. 3 shows three gel autoradiograms
A (without peptide substrate)
B (with acryl-peptide substrate)
C (with acetyl-peptide substrate)

The following samples were given into the tracks:

| Track 1: | marker of molecular weight (non-radioactive!) |
|---|---|
| Track 2: | PKA 100 pg |
| Track 3: | PKA 50 pg |
| Track 4: | PKA 25 pg |
| Track 5: | PKA 12.5 pg |
| Track 6: | PKA 6.25 pg |
| Track 7: | PKA 3.13 pg |
| Track 8: | PKA 1.56 pg |
| Track 9: | empty |
| Track 10: | CCE 14.55 µg |
| Track 11: | CCE 7.28 µg |
| Track 12: | CCE 3.64 µg |
| Track 13: | CCE 1.28 µg |

It is only possible to detect a band in the autoradiogram at the position at which the catalytical subunit of the cAMP dependent protein kinase having a molecular weight of 42 000 Dalton is expected in tracks 2 to 8 of gel B. The intensity of the band decreases as the amount of applied enzyme decreases. A large number of bands are detected in tracks 9 to 12 of all three gels where the CCE cell extract was applied. Here, mainly autophosphorylation is observed for which no additional substrate is required. Again, the intensity of the bands decreases as the amount of applied protein decreases. However, only in gel B into which the acryl-peptide was polymerized the intensity of the band does not decrease as quickly as the other bands at the height of PKA. More substrate can be phosphorylized here because additional peptide/substrate is present.

These experiments unambiguously show that the M-Sp-Sub product is retained in the gel and can be converted by the enzyme as a substrate.

In principle, this method can be used for a variety of other enzyme activities, e.g., for polynucleotide kinases: in this case, the substrate would be a synthetic or natural DNA fragment or oligonucleotide; again, detection of the activity could be achieved by incorporation of radioactively labelled phosphate of [γ-$^{32}$P] ATP.

proteases: in this case, the substrate would be a synthetic peptide; the detection of activity could be achieved, e.g., by fluorescence detection if the peptide substrate has two fluorophores which quench each other and which are separated from each other when the peptide is cleaved (M. Meldal and I. Svendsen, 1995, J. Chem. Soc. Perkin Trans. I, Vol. 1996, pp. 1591–1596).

phosphatases: in this case, the substrate would be, e.g., a radioactive phosphorylated peptide; the detection of activity could be achieved by cleaving the label and detecting the decrease in radioactivity at the position of the enzyme.

Many other examples can be construed in which the substrate which is covalently bound to the gel is either detected in a labelled form or the label present is destroyed by the enzyme reaction.

Kinase Tests in the Gel After 2D-electrophoresis

First dimension: Isoelectric focussing

For conducting the kinase tests in the gel, membrane-enriched cell extracts were isoelectrically focussed on IPG strips having a length of 18 cm (pH 3–10) in the first dimension by 300 kVh and subsequently prepared for size separation in the second dimension using a DTT-containing equilibration solution (15 min.).

The following substrates were polymerized into the gel:

EGF-receptor kinase-substrate: acryl-AEGSAYEEV-COOH

PKC-substrate: acryl-RRRRRKGSFRRKA-COOH

PKA-substrate: acryl-ARALRRASLG-$NH_2$

Approximately 1 nmol substrate (=approx. 1–2 mg) was used per gel (20 ml volume), respectively.

After pouring the gels onto gel bond film the gels were soaked in water and subsequently equilibrated with SDS analytical buffer (pH 8.6). Before conducting SDS-PAGE, the region of the spacer gel was equilibrated with spacer gel buffer (pH 6.8). The rinsing steps are to remove unpolymerized rests of acrylamide. The IPG strips were put on the peptide-containing gels. Gel electrophoresis was conducted for approx. 6 hours in an horizontal position.

Renaturation step (according to Kameshita and Fujisawa, Anal. Biochem., 1989, Vol. 183, pp. 139–143; modified)

| | | |
|---|---|---|
| 1. | removal of SDS using 20% isopropanol in 50 mM Tris, pH 8.0 | 2 × 30 min. |
| 2. | equilibration using 50 mM Tris, pH 8.0, 5 mM DTT | 1 h, RT |
| 3. | denaturation using 6M guanidine-HCi in 50 mM Tris, pH 8.0, 5 mM DTT | 1 h, RT (2 changes) |
| 4. | renaturation using 50 mM Tris, pH 8.0, 5 mM DTT, 0.04% Tween 20 | 16 h, 4° C. (5 changes) |
| 5. | equilibration using kinase test buffer 50 mM MOPS, pH 6.9, 0.4 mM EGTA, 2 mM DTT, 20 mM $MgCl_2$, 100 mM NaCl | 30 min., 30° C. |
| 6. | kinase test using fresh kinase test buffer 150 ml including 25 μM ATP and 1.8 mCl [$\gamma$-$^{32}$P] ATP | 45 min., 30° C. |
| 7. | stopping the reaction and washing with 5% TCA and 1% Na-pyrophosphate | approx. 20 h or until only a small amount of activity is detected in the washing solution |
| 8. | dyeing the gels, drying and phosphoimaging | approx. 10 days |

Figure 4:
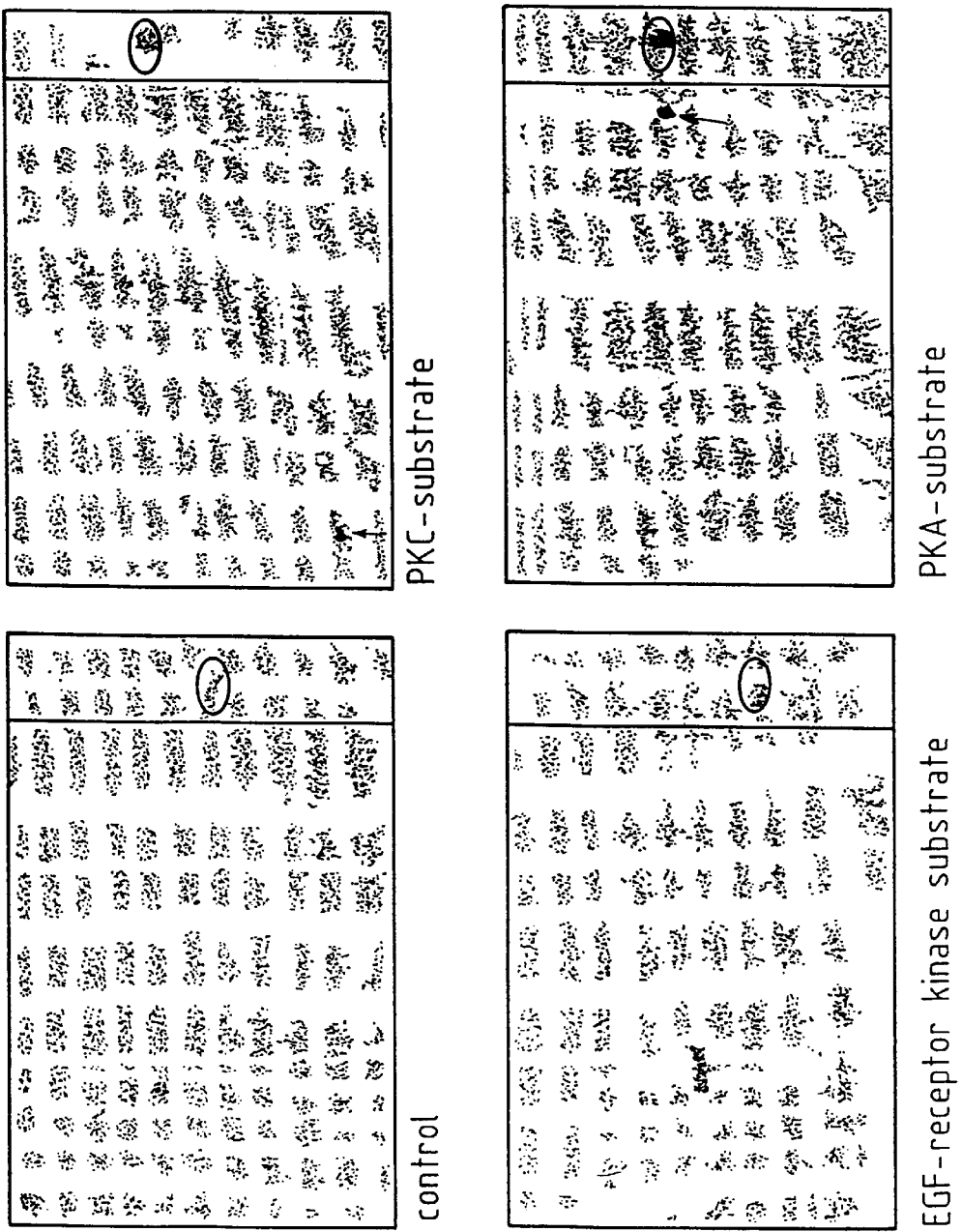

The results are shown in FIG. 4. The control does not contain any substrate. Right strips: on each gel approx. 2 μg PKA were applied to the right of the IPG strips to check the renaturation step. The enzyme was active, phosphorylated both basic peptides well and exhibited little autophosphorylation (control without substrate) and tended to be inhibited by the EGF receptor kinase substrate.

What is claimed is:

1. A method for separating and detecting protein kinase activities by conducting the following steps in the given order:
   (a) covalently binding a substrate to a monomeric or oligomeric constitutional unit of a gel;
   (b) polymerizing the resultant product to form a gel matrix of a separating gel;
   (c) electrophoretically separating the protein kinase activities to be separated using the separating gel, and optionally renaturating; and
   (d) detecting, either by labelling with a detectable label or destroying a label present, by reacting the substrate which is covalently bound in the gel with the separate protein kinase activity/activities.

2. The method according to claim 1, wherein the substrate comprises a natural or synthetic peptide, a natural or synthetic oligonucleotide or a small organic molecule.

3. The method according to claim 1, wherein before polymerization the product prepared from the constitutional unit of substrate and gel is mixed with constitutional unit comprises acrylic monomers, acrylic acid oligomers, methacrylic acid monomers and/or methacrylic acid oligomers.

4. The method according to claim 1, wherein the constitutional units of the gel of gel which do not contain substrate molecules.

5. The method according to claim 1, wherein the polymerization method is solution or bulk polymerization.

6. The method according to claim 1, wherein a spacer is incorporated between the substrate and the monomeric or oligomeric constitutional unit of the gel.

7. The method according to claim 6, wherein the spacer comprises a natural or synthetic peptide, a natural or synthetic oligonucleotide or a small organic molecule.

8. A method of separating and detecting protein kinase activities by conducting the following steps in the given order:
   (a) using a separating gel which is obtained by covalently binding a substrate to a monomeric or oligomeric constitutional unit of a gel and polymerizing the resultant product to form a gel matrix of a separating gel;
   (b) electrophoretically separating the protein kinase activities to be separated using the separating gel, optionally renaturating; and
   (c) detecting, either by labelling with a detectable label or destroying a label present, by reacting the substrate which is covalently bound in the gel with the separate protein kinase activity/activities.

9. The method according to claim 8, wherein the substrate comprises a natural or synthetic peptide, a natural or synthetic oligonucleotide or a small organic molecule.

10. The method according to claim 8, wherein before polymerization the product prepared from the constitutional unit of substrate and gel is mixed with constitutional unit comprises acrylic monomers, acrylic acid oligomers, methacrylic acid monomers and/or methacrylic acid oligomers.

11. The method according to claim 8, wherein before polymerization the product prepared from the constitutional unit of substrate and gel is mixed with constitutional units of gel which do not contain substrate molecules.

12. The method according to claim 8, wherein the polymerization method is solution or bulk polymerization.

13. The method according to claim 8, wherein a spacer is incorporated between the substrate and the monomeric or oligomeric constitutional unit of the gel.

14. The method according to claim 13 wherein the spacer comprises a natural or synthetic peptide, a natural or synthetic oligonucleotide or a small organic molecule.

* * * * *

SEQUENCE LISTING

<160> NUMBER OF SEQ ID NOS: 3

<210> SEQ ID NO 1
<211> LENGTH: 10
<212> TYPE: PRT
<213> ORGANISM: artificial sequence
<220> FEATURE:
<223> OTHER INFORMATION: description of the artificial sequence: artificial peptides

<400> SEQUENCE: 1

Ala Arg Ala Leu Arg Arg Ala Ser Leu Gly
1               5                   10

<210> SEQ ID NO 2
<211> LENGTH: 9
<212> TYPE: PRT
<213> ORGANISM: artificial sequence
<220> FEATURE:
<223> OTHER INFORMATION: description of the artificial sequence: artificial peptides

<400> SEQUENCE: 2

Ala Glu Gly Ser Ala Tyr Glu Glu Val
1               5

<210> SEQ ID NO 3
<211> LENGTH: 13

```
<212> TYPE: PRT
<213> ORGANISM: artificial sequence
<220> FEATURE:
<223> OTHER INFORMATION: description of the artificial sequence:
      artificial peptides

<400> SEQUENCE: 3

Arg Arg Arg Arg Arg Lys Gly Ser Phe Arg Arg Lys Ala
 1               5                  10
```